United States Patent [19]

Weidlich

[11] Patent Number: 5,332,908
[45] Date of Patent: Jul. 26, 1994

[54] METHOD FOR DYNAMIC BEAM PROFILE GENERATION

[75] Inventor: Georg A. Weidlich, Concord, Calif.

[73] Assignee: Siemens Medical Laboratories, Inc., Concord, Calif.

[21] Appl. No.: 17,459

[22] Filed: Feb. 11, 1993

Related U.S. Application Data

[63] Continuation of Ser. No. 860,945, Mar. 31, 1992, abandoned.

[51] Int. Cl.⁵ ............................................. G21K 1/04
[52] U.S. Cl. .................................. 250/492.1; 378/65; 378/152; 250/505.1
[58] Field of Search ............... 250/492.1, 505.1, 492.3; 378/65, 152, 151

[56] References Cited

U.S. PATENT DOCUMENTS

| | | |
|---|---|---|
| 4,027,167 | 5/1977 | Pollermann . |
| 4,109,154 | 8/1978 | Taumann ............................ 250/503 |
| 4,140,129 | 2/1979 | Heinz et al. ......................... 128/404 |
| 4,343,997 | 8/1982 | Heinz ............................... 250/505.1 |
| 4,359,642 | 11/1982 | Heinz et al. ......................... 378/150 |
| 4,380,820 | 4/1983 | Cutter . |
| 4,581,753 | 4/1986 | Rice . |
| 4,672,652 | 6/1987 | Hüttenrauch et al. . |
| 4,754,147 | 6/1988 | Maughan et al. . |
| 4,817,125 | 3/1989 | Sklebitz . |
| 5,008,907 | 4/1991 | Norman et al. . |
| 5,019,713 | 5/1991 | Schmidt ............................ 250/492.3 |

OTHER PUBLICATIONS

"Automatic Variation of Field Size and Dose Rate in Rotation Therapy", Mantel et al., 2 J. Radiat. Oncol. Biol. Phys. 697 (1977), pp. 697–704.

"Wedge Shaped Dose Distribution by Computer Controlled Collimator Motion", Kijewski et al., 5 Med. Phys. 426 (1978), pp. 426–429.

"Computer Controlled Radiation Therapy", Levene et al., 129 Radiol. 769, (1978), pp. 769–775.

"Dose Optimization with Computer Controlled Gantry Rotation, Collimator Motion and Dose Rate Variation", Chin et al., 9 J. Radiat. Oncol. Biol. Phys. 723 (1983), pp. 723–729.

*Primary Examiner*—Jack I. Berman
*Attorney, Agent, or Firm*—Lawrence C. Edelman

[57] ABSTRACT

A method for applying a radiation treatment with an arbitrary isodose profile is disclosed. The treatment apparatus has a radiation source which generates a radiation beam with an axis. The apparatus also includes a collimator having a plurality of independently movable plates disposed in the path of the radiation beam and oriented in a direction perpendicular to said beam axis. Each set has two movable plates. Control signals are generated. Two plates within a set of plates are actuated independently in orthogonal directions during the treatment, in response to the control signals, causing the beam to change in width. The intensity of the beam is changed as a function of the position of the plates to generate an arbitrary beam profile. Exemplary profiles which may be generated included rotationally symmetric parabolic profiles and flat profiles.

17 Claims, 5 Drawing Sheets

METHOD FOR DYNAMIC BEAM PROFILE GENERATION

CROSS-REFERENCE TO RELATED APPLICATION

This is a continuation of Ser. No. 07/860,945 filed Mar. 31, 1992, now abandoned. Furthermore, Ser. No. 07/860,959 filed Mar. 31, 1992 is a related application.

BACKGROUND OF THE INVENTION

1. Field of the Invention

This invention relates to the field of linear accelerators, and in particular to computer controlled radiation therapy systems.

2. Description of the Prior Art

Radiation therapy has been used extensively as a method for treating cancer patients, either alone, or in combination with surgery and chemotherapy. In typical radiation therapy systems, such as the Mevatron systems available from Siemens Medical Systems, Inc. (Iselin, N.J.), a radiation source is housed in a structure called a gantry. The apparatus includes a conventional microwave power source such as a klystron, and an accelerator structure, which may be a travelling wave or standing wave device. The accelerator produces an electron beam, which is steered through a collimating head mounted on the gantry and directed at the region to be treated. For more superficial tumors, the electron beam itself is used for treatment, because it has less impact on deeper tissue. For deeper tumors, however, high energy X rays are preferred for their penetrating power. To generate the X rays, the same electron accelerator may be used with the addition of a target made of heavy metal (e.g., gold or tantalum) placed in the path of the electron beam. The target emits a continuous X ray Bremsstrahlung spectrum when struck by the electron beam.

The gantry can rotate about a gantry axis which extends from the head to the foot of a treatment couch on which the patient lies, so that the radiation can enter the patient from different angles. The radiation beam coming from the accelerator is always directed through, and centered on, the gantry axis.

In applying radiation to the patient, two competing objectives are present: eliminating the malignant cells in the target region, and avoiding complications due to application of radiation to surrounding tissues. To avoid these complications, lower doses have often been applied to the targeted tumor cells than would be applied if complications were not considered, lowering the probability of successful cancer elimination. To protect surrounding tissues without compromising the treatment, it is desirable to tailor the radiation dosage to match the size, shape and location of the malignant region.

Several methods have been used in radiation therapy systems to improve control of the dosage distribution. One such method is to shape the beam profile. The "raw" beam which leaves the target has a non-uniform intensity. It is known to balance or compensate the dosage in any given space-angle range of the radiation leaving the target by placing a compensating absorber in the beam path. U.S. Pat. No. 4,109,154 to Taumann discusses an electron accelerator in which a compensating absorber is used to shape the beam profile. The absorber absorbs overly intense radiation in the center of the beam cone.

A paper by Mantel, et al. entitled "Automatic Variation of Field Size and Dose Rate in Rotation Therapy" 2 J. Radiat. Oncol. Biol. Phys. 697 (1977) discusses a technique for changing the field size and dose rate used during rotation therapy. The gantry (and the enclosed beam forming head) rotates around the patient, so that the beam is applied from several angles. The field size and dose rate are varied as functions of the gantry angle. In this technique, the field size is adjusted in one dimension by moving a set of collimator aperture plates, or jaws, which define the beam aperture (and control the beam width), and simultaneously varying the dose rate during rotation in accordance with values selected by a computer program. The result is a more uniform dose distribution inside the target volume, and reduced dose outside that volume.

U.S. Pat. No. 4,140,129 to Heinz et al discloses a beam defining system for an electron accelerator, having an adjustable collimator and an accessory holder, to which an electron applicator is attached. The electron applicator has a wall which encloses the electron beam cone from the collimator, and an additional frame-shaped limiting aperture in order to limit the electron beam cone at the edges which face away from the beam defining system. The scattered or secondary electrons in the marginal region of the beam cone are substantially blocked by the limiting aperture. The electrons which are thus blocked have lower energy levels and, so, do not contribute to higher dosage performance deep within the patient. Thus, this device reduces undesirable irradiation of the skin surrounding the target.

U.S. Pat. Nos. 4,343,997 and 4,359,642 to Heinz, which are hereby incorporated by reference for their teachings on radiation treatment devices, describe a collimator assembly which may be used to limit or define X-ray cones of various sizes in an electron beam accelerator. A flattening filter is used with this technique to flatten the X-ray density profile. Flat dosage is achieved through the use of a collimator shielding block and one of a plurality of insert pieces or bushings which are interchangeable with one another to produce different cone angles for irradiating different sized areas.

Figure 2A:
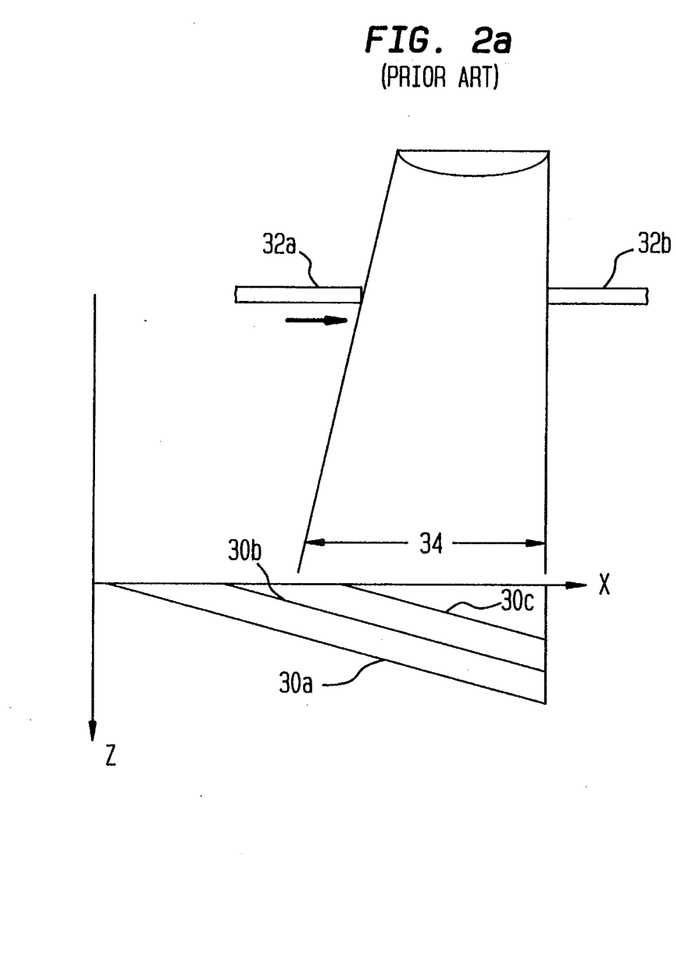
FIGS. 2a and 2b are graphs of radiation intensity versus distance which show typical wedge shaped isodose profiles produced by prior art systems.
Figure 2B:
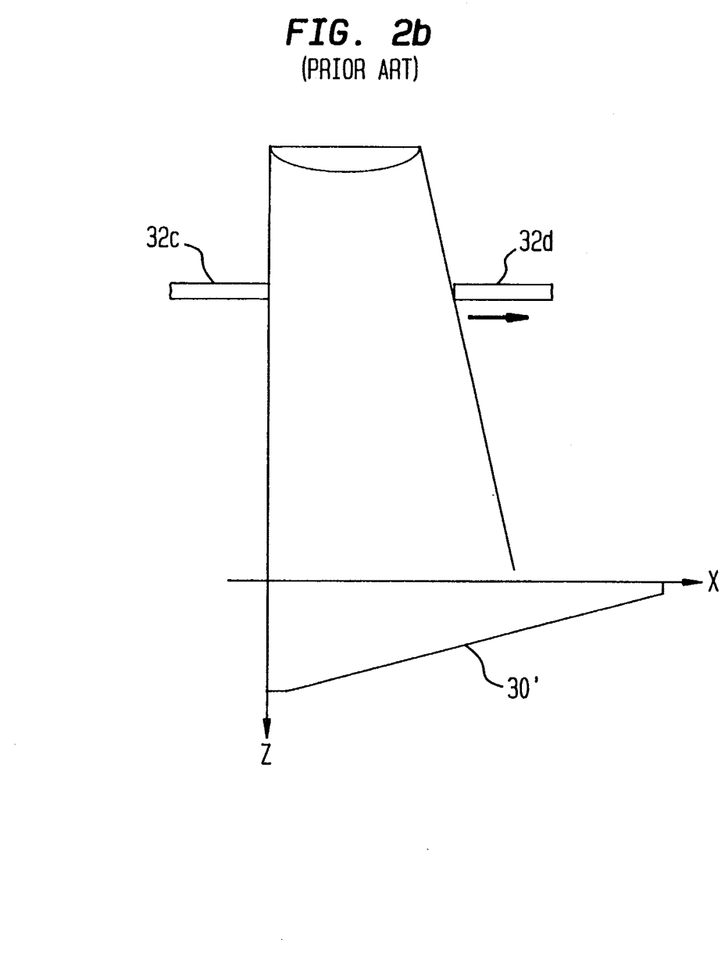

Another method of controlling the dosage profile is to vary the size of the beam aperture. A paper by Kijewski, et al. entitled, "Wedge shaped Dose Distribution by Computer Controlled Collimator Motion" 5 Med. Phys. 426 (1978) discusses the use of a defined plate (jaw) motion to obtain a wedge-shaped isodose curve (the set of points which receive the same dose of radiation) during irradiation. FIG. 2a shows isodose profiles 30a–c achieved by this technique. The treatment begins with two collimator plates 32a, 32b separated from one another. After a predetermined time interval, plate 32a is moved towards plate 32b, which remains stationary. The movement continues until the plates meet. This causes the beam width 34 to become narrower as the treatment continues. The isodose curves 30a–c are deeper in the region near the stationary plate, which is exposed to radiation the longest. Such wedge shaped isodose curves may be desired in radiation therapy to adjust to anatomical conditions of the subject. A similar result may be achieved by beginning with closed plates and opening the plates. FIG. 2b shows an isodose curve in which the plates 32c, 32d begin in the closed position.

U.S. Pat. No. 5,019,713 to Schmidt discusses a radiation therapy device in which a movable aperture assembly and a non-movable filter body are combined to allow the isodose curve in the object of irradiation to rise or fall in the opening direction. At the beginning of the treatment, the plates are closed, and one plate begins to move away from the other (stationary) plate. The absorptance of the filter varies across its length. The cumulative radiation dose received at any point varies as a function of both the filter characteristics and the distance from the stationary plate, making possible non-monotonic isodose curves which vary in one dimension. For example, if the portion of the filter closest to the stationary plate has a higher absorptance, the isodose curve will have an inverted U-shape.

A paper by Levene, et al. entitled, "Computer Controlled Radiation Therapy" 129 Radiol. 769 (1978) discusses variation of dose rate, gantry angle and collimator plate position to achieve the known "arc wedge" technique. A paper by Chin et al. entitled, "Dose Optimization with Computer Controlled Gantry Rotation, Collimator Motion and Dose Rate Variation" 9 J. Radiat. Oncol. Biol. Phys. 723 (1983) discusses methods by which continuous irradiation is simulated by summation of a large number of discrete stationary beams. Dose rate, gantry angle and collimator plate positions are varied among the beams. These methods achieve isodose contours which might not be attainable using a single stationary beam.

It is noted that the Levene et al. and Chin et al. papers relate to a conformal radiation treatment which conforms the field profile and dose rate to a target volume using gantry rotation.

While some of these devices can produce a number of different radiation contours, the apparatus and methods used may be relatively cumbersome and time consuming.

SUMMARY OF THE INVENTION

In accordance with the present invention, an exemplary system and method are provided for controlling the isodose profile of radiation treatment apparatus, in order to provide a rotationally symmetric profile. The system includes an electron accelerator which generates a photon beam. The accelerator has a collimator assembly operating under computer control. The collimator assembly includes a plurality of movable plates mounted to a rotatable collimating head. The plates are oriented in a direction perpendicular to the longitudinal axis of the beam, so that the beam width is defined by the relative positions of the plates.

The plates are actuated during the radiation treatment, under computer control, to vary the beam width defined by the opening formed between the plates according to a predetermined plate motion function which is both continuous and continuously derivable to achieve a desired beam profile without rotation of the longitudinal axis of the beam.

According to one aspect of the invention, the treatment is divided into two parts. During each part, two movable plates are first moved together from an open position, and then opened from a closed position or vice-versa. The direction of motion of the plates during the second part of the treatment is perpendicular to the direction of plate motion during the first part. This may be accomplished by rotating the collimating head ninety degrees at the completion of the first part of the treatment, or by using a second set of movable plates, which are orthogonal to the first set.

According to a second aspect of the invention, a different set of plate movements are used to generate a beam profile with a flat isodose curve, without the use of a flattening filter. This is accomplished by opening the plates from the edge of the treatment region towards the center axis on each side of the beam axis. The same sequence is repeated using the second set of collimator plates, which move in a perpendicular direction. In a further exemplary embodiment, instead of using the second set of plates, the collimator is rotated ninety degrees and the series of plate movements are repeated using the first set of plates.

BRIEF DESCRIPTION OF THE DRAWINGS

FIG. 1b is a cross-sectional view, taken perpendicular to the beam axis which shows the beam-defining jaws of the system shown in FIG. 1a.

FIG. 4 is a graph of an isodose curve (102) and radiation intensity versus distance (100) which shows the unfiltered beam profile produced by the system shown in FIG. 1a.

FIGS. 5b and 5c are cross-sectional views, taken perpendicular to the beam axis which show the motion of the beam-defining jaws used to produce the beam profile shown in FIG. 5a.

DETAILED DESCRIPTION

Figure 1A:
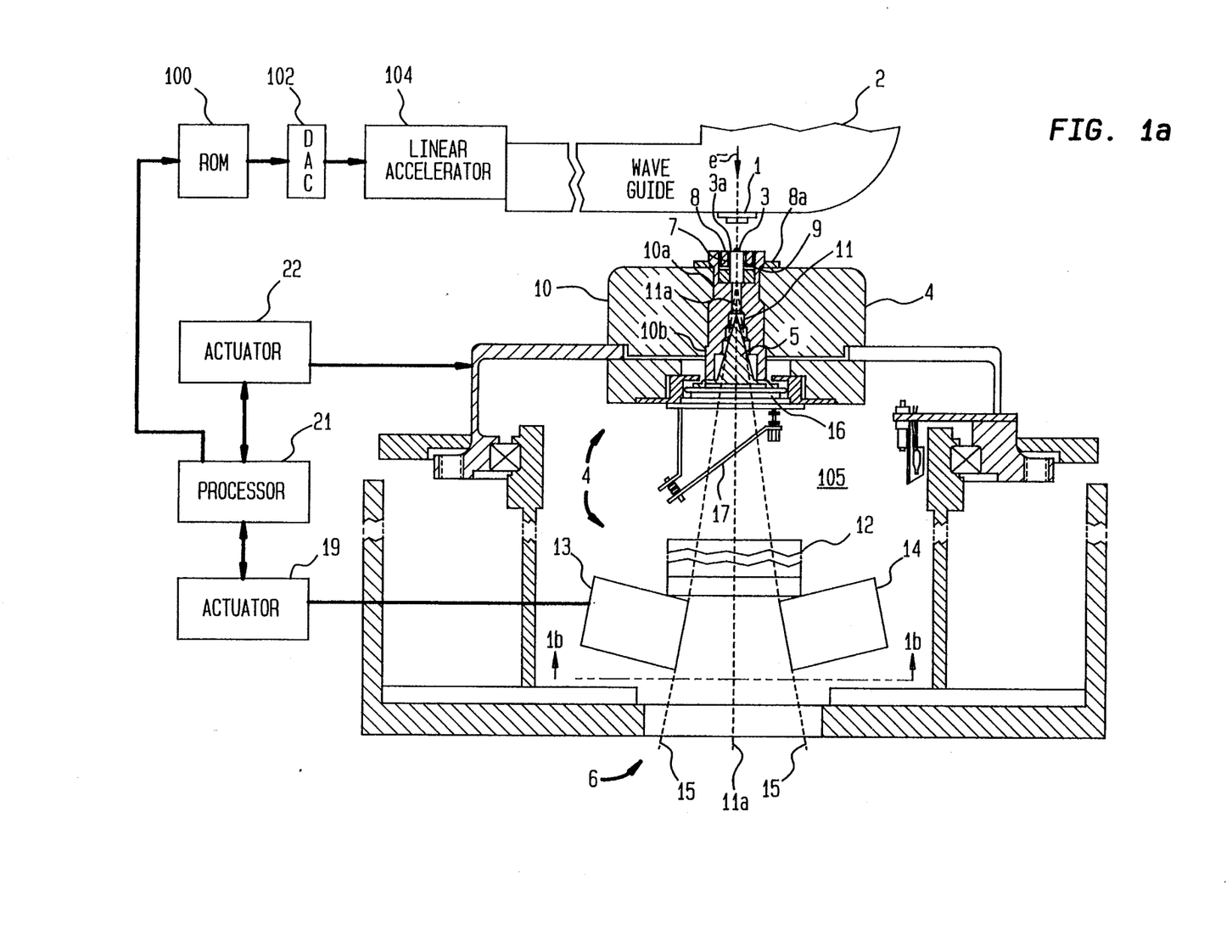
FIG. 1a is a cross-sectional view, partly in block diagram form of a beam defining system of radiation treatment apparatus which includes an embodiment of the present invention.

FIG. 1 shows an exemplary embodiment of the beam defining system 6 of a medical linear accelerator in accordance with the present invention. An electron accelerator which includes a linear accelerator 104 and a standing wave guide 2 has an exit window 1, through which an electron beam e− is transmitted to a collimator assembly 105. The collimator assembly 105 includes a target 3 and electron absorber 9 for generating an X ray beam. The generated beam is substantially free of unabsorbed electrons. The target 3 and absorber 9 are mounted within a carrier plate 8 of the assembly 105. The target 3, absorber 9 and carrier plate 8 may be removed from the apparatus if desired, to use the electron beam itself for treatment (e.g., for superficial treatment) instead of X rays. The term radiation beam will be used to refer to either an electron beam or an X ray beam.

The intensity of the electron beam and thus of the X ray beam is controlled by the processor 21. In response to address values provided by the processor 21, a read-only memory (ROM) 100 applies programmed digital values to a digital-to-analog converter (DAC) 102. The DAC 102 converts the digital values into control voltages for the linear accelerator 104. In response to different control voltages values, the linear accelerator produces bursts of electrons at respectively different pulse rates (commonly referred to as PRF). Bursts produced at a relatively high rate generate a more intense beam of radiation (i.e. a higher dose rate) than bursts at a relatively low rate. In the exemplary embodiment of the invention, the processor 21 controls the intensity of the X ray beam during a treatment to generate different beam profiles.

The radiation beam has a central axis 11a. The beam collimating block 4 is disposed in the path of the radiation, directly below the carrier plate 8. The beam collimating block includes a thick walled collimator shielding block or collimator 10. The collimator 10 houses an insert 10a, to which a flattening filter 5 may be mounted. The flattening filter 5, when used, symmetrically attenuates the radiation more towards the center of the beam, so that the intensity of the radiation is approximately constant across the beam width. Filter 5 is rotationally symmetric and is centered relative to axis 11a.

The collimator assembly 105 has two pairs of tungsten X ray shielding plates, 12a, 12b, and 13, 14 which are adjustable relative to the axis 11a. In the system shown in FIG. 1a, plate 12a (not visible in the Figure) moves into the page while plate 12b moves out of the page. Plates 13 and 14 move to the left and right respectively. Thus, each pair of plates 12a, 12b and 13, 14 is movable along a single axis, referred to as the X and Y axes, respectively. The X and Y axes and the beam axis 11a form an orthogonal set. The inner edges of the plates define the radiation field edge, and therefore, the positions of the four plates determine the radiation field size. The plates 12a, 12b, 13 and 14 are shown in a view along the Z axis in FIG. 1b. At least two of the plates are capable of crossing axis 11a. The collimator is mounted for rotation about the beam axis.

In order to provide the desired accuracy for the speed and position of the collimator plates 12, 13, 14, the plate positions are controlled by an automatic drive unit 19 under computer 21 control. This drive unit may be, for example, a conventional numerically controlled servo system which may use either conventional servo motors or stepper motors to control the positions of the jaws 12a, 12b, 13 and 14.

In the exemplary embodiment of the invention, the computer 21 periodically calculates a desired position for at least one of the laws 12a, 12b, 13 and 14 and applies the desired position to the actuator 19. The actuator, in turn, moves the jaw to the desired position. Using this control scheme, a wide variety of beam profiles may be generated which employ both linear and non-linear jaw-motion functions.

In addition, the processor 21 may cause the entire collimator assembly 105 except for the collimating block 4 to rotate by 90° (i.e. counter-clockwise out of the page) and then back to 0° by activating actuator 22.

The invention includes a method for producing a beam with an arbitrary two dimensional isodose contour. An isodose contour is the locus of points in three dimensional space which receive the same total dosage of radiation. The isodose contour is the three dimensional analog of the two dimensional isodose curve.

In some of the embodiments of the invention described below, the apparatus used is as described above, with the flattening filter installed in the collimator. With this filter in place, the beam leaving the collimator is of substantially uniform intensity in both the X and Y directions. Other embodiments of the invention produce a substantially flat beam profile without using a flattening filter.

In order to determine the plate movements which result in the desired dosage being applied, a coordinate system is adopted in which the X and Y axes are located in a plane parallel to the surface of the object which is to be irradiated. The Z axis coincides with the longitudinal axis of the beam and the positive Z direction is the direction of the beam (i.e., pointing from the radiation source towards the treatment area). One set of plates moves in a direction parallel to the X axis and the other set of plates moves in the direction parallel to the Y axis. Equation (1) gives the dosage received for any point (x,y) on the surface at any depth z below the irradiated surface. The attenuation of a two dimensional beam is therefore described by equation (1).

$$D_{(x,y)} = D_{0(x,y)} e^{-\mu z} \tag{1}$$

where:
  z = Depth
  $D_{0(x,y)}$ = Dose deposited at the surface at point (x, y)
  $D_{(x,y)}$ = Dose deposited at depth z below point (x,y)
  $\mu$ = Linear attenuation coefficient for the object irradiated For an isodose contour (i.e., $D_{(x,y)}$ = a constant), equation (1) may be solved for the surface beam dosage profile, yielding equation (2).

$$D_{0(x,y)} = D_a e^{\mu z(x,y)} \tag{2}$$

where:
  $z_{(x,y)}$ = Depth of the isodose contour at (x,y), measured in the z direction
  $D_a$ = Dosage on the isodose contour Equation (2) is differentiated with respect to time in order to determine the dosage rate to be applied to each point to achieve the desired dose profile. Taking the total derivative of equation (2), and simplifying yields equation (3).

$$D_{0(x,y)} = \left| D_a \mu e^{\mu z(x,y)} \left( v_x \frac{d}{dx} [z(x,y)] + v_y \frac{d}{dy} [z(x,y)] \right) \right| \tag{3}$$

where:
  $D_{0(x,y)}$ = Total dosage rate at the surface at point (x,y)
  $v_x$ = dx/dt = relative plate velocity in the X direction
  $v_y$ = dy/dt = relative plate velocity in the Y direction For an isodose contour with an arbitrary shape, the contour $z_{(x,y)}$ will be a function of both X and Y. In order to apply equation (3) for such an isodose contour, the irradiated surface may be divided into a two dimensional array of treatment areas, where an independent radiation field is applied to each area.

To apply the radiation to one of these areas, one set of collimator plates 13, 14 is held still, while the plates 12 in the second pair are moved relative to one another to produce, for example, a wedge shaped area isodose contour. For any area with a flat isodose contour, both sets of plates are held still. For each of these areas, a dosage profile (e.g., constant or wedge shaped) is applied, to approximate the desired isodose contour with a function that is piecewise continuous. This dosage profile may have discontinuities in its derivative at the edges of each treatment area, depending on the profile within each area.

The dosage profile may also be changed by changing the intensity of the beam provided by the linear accelerator 104 and wave guide 2. As set forth above, this occurs when the processor 21 changes the address value applied to the ROM 100, thereby changing the PRF of the bursts applied to accelerator 104.

The method described above for an arbitrary isodose contour may be time consuming if the number of treatment areas is very large. Depending on the nature of the isodose profile in each area, the collimator plates may have to be repositioned when treatment of each area is begun. The method is useful, however if extremely tight control of the isodose contour is desired.

The first exemplary embodiment of the invention includes a method for generating a large and useful class of isodose contours for which the number of independent treatment areas is one. That is, the radiation may be applied in a two part treatment consisting of only one set of plate movements in the X direction and one set of movements in the Y direction. While the first pair of plates is moving in the X direction, the plates oriented parallel to the Y axis remain still (i.e., Y=a constant). Similarly, while the second pair of plates is moving in the Y direction, the plates oriented parallel to the X axis remain still (i.e., X=a constant). Further, to simplify the demands made on the equipment configuration, the plate motions are limited so that the plate speed and the beam intensity variations are continuous functions of time within each of the two sections of the treatment. Any contour which can be described by equation (4) falls into this category.

$$z(x,y) = z_1(x) + z_2(y) \tag{4}$$

where:

$z_1(x) =$ a function of x only
$z_2(y) =$ a function of y only

Substituting equation (4) into equation (2) and taking the time derivative yields equation (5).

$$D_{0(x,y)} = \left| D_a \mu e^{\mu z_1(x)} e^{\mu z_2(y)} \left( v_x \frac{d}{dx} z_1(x) + v_y \frac{d}{dy} z_2(y) \right) \right| \tag{5}$$

It is desirable to separate equation (5) into two equations, each of which involves only a single variable. If x is held constant, then:

$$e^{\mu z_1(x)} = \text{a constant.} = b_x \tag{6}$$

If y is held constant, than $$e^{\mu z_2(y)} = \text{a constant.} = b_y \tag{7}$$

Equation (5) can then be written as follows:

$$D_{0(x,y)} = D_{1(x)}|_{y=const.} + D_{2(y)}|_{x=const.} \tag{8}$$

where:

$$D_{1(x)}|_{y=const.} = C_1 e^{\mu z_1(x)} v_x \frac{d}{dx} z_1(x) \tag{9}$$

$$D_{2(y)}|_{x=const.} = C_2 e^{\mu z_2(y)} v_y \frac{d}{dy} z_2(y) \tag{10}$$

-continued

For any desired isodose contour which can be expressed as the sum of a function of only X plus a function of only Y, equations (8), (9) and (10) may be used to define a treatment which is applied in two distinct parts, one including plate motion in the X direction for a fixed Y direction plate opening, and the other including motion in the Y direction for a fixed X direction plate opening. For each contour, the intensity of the radiation beam applied by the processor 21 is determined by the equations (9) and (10).

An example of such a contour is one in which there is rotational symmetry about the beam axis. For such an isodose contour, any cross section which is perpendicular to the beam axis (i.e., constant depth, z) will be a circle. Such an isodose contour is described by equation (11), in which the locus of points for any fixed value of z define a circle.

$$z(x,y) = C_3 - ax^2 - ay^2 \text{ for all x,y} \tag{11}$$

In equation (11), the values of $C_3$ and "a" are determined from the boundary conditions for a particular isodose contour. In the exemplary embodiment, $C_3$ is the depth of the isodose curve at beam axis (X=0, Y=0).

It is desirable to express equation (11) in a form which can be combined with equations (4). Equations (12), (13) and (14) describe an isodose contour which is separable into functions of X only and Y only, and which have circular cross sections, defining rotational symmetry, consistent with equation (11).

$$z_1(x) = -ax^2 + c_x \tag{12}$$

$$z_2(y) = -ay^2 + c_y \tag{13}$$

$$C_3 = c_x c_y \tag{14}$$

where $c_x$ and $c_y$ are constants

Figure 3A:
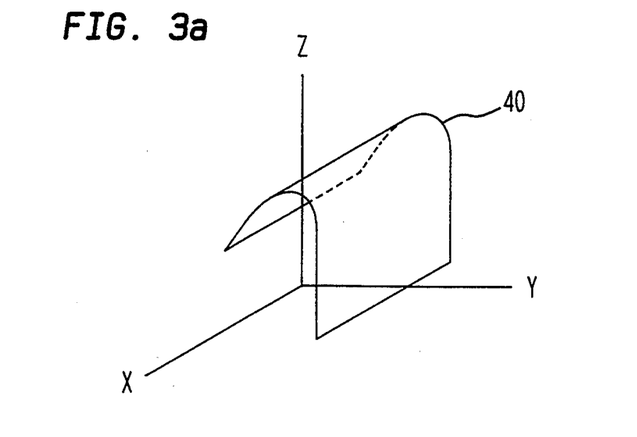
FIGS. 3a and 3b are graphs of radiation intensity versus distance which show exemplary parabolic isodose profiles that may be generated by the system shown in FIG. 1.
Figure 3B:
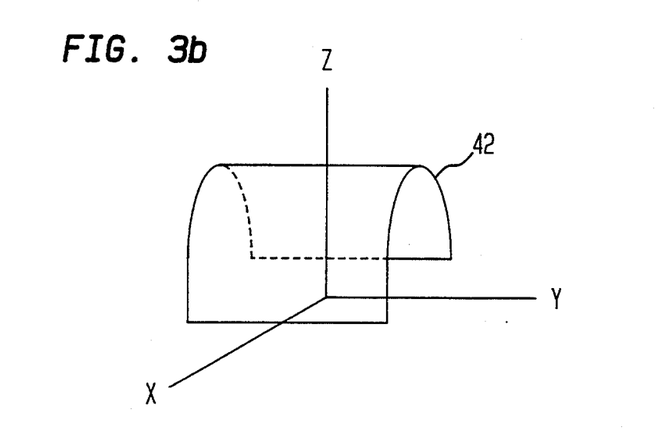
Figure 3C:
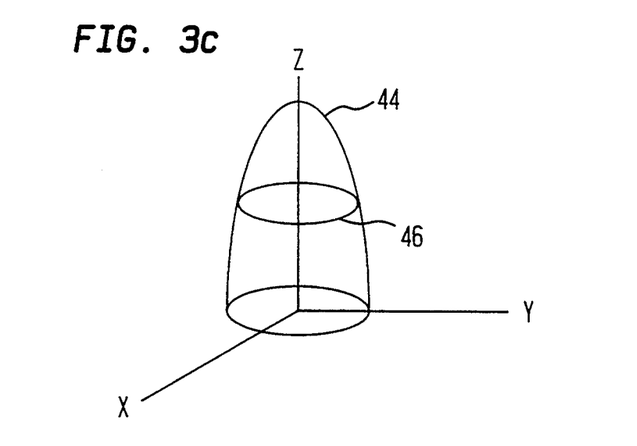
FIG. 3c is a graph of radiation intensity versus distance which shows the effective isodose profile formed by summing the profiles shown in FIGS. 3a and 3b.

Equation (12) defines parabolas in planes parallel to the plane including the X and Z axes. FIG. 3b shows an isodose contour 42 of this form. Any cross section of contour 42 parallel to the X-Z plane is a parabola. Similarly, equation (13) defines parabolas in planes parallel to the plane including the Y and Z axes. FIG. 3a shows an isodose contour 40 of this form. FIG. 3c shows the isodose contour 44 which is produced by summing the two treatments, with circular cross section 46. Equations (12) and (13) can be substituted into equations (9) and (10), yielding the desired governing equations (15) and (16) for the beam intensity in terms of the plate motions.

$$D_{1(x)}|_{y=const.} = D_a \mu b_y e^{\mu(-ax^2+cx)} * (2ax v_x) \tag{15}$$

$$D_{2(y)}|_{x=const.} = D_a \mu b_x e^{\mu(-ay^2+cy)} * (2ay v_y) \tag{16}$$

Equations (15) and (16) provide the desired relationship between the plate position and velocity and the corresponding intensity of the radiation beam (dose rate) which produce a rotationally symmetric beam profile.

Figure 1B:
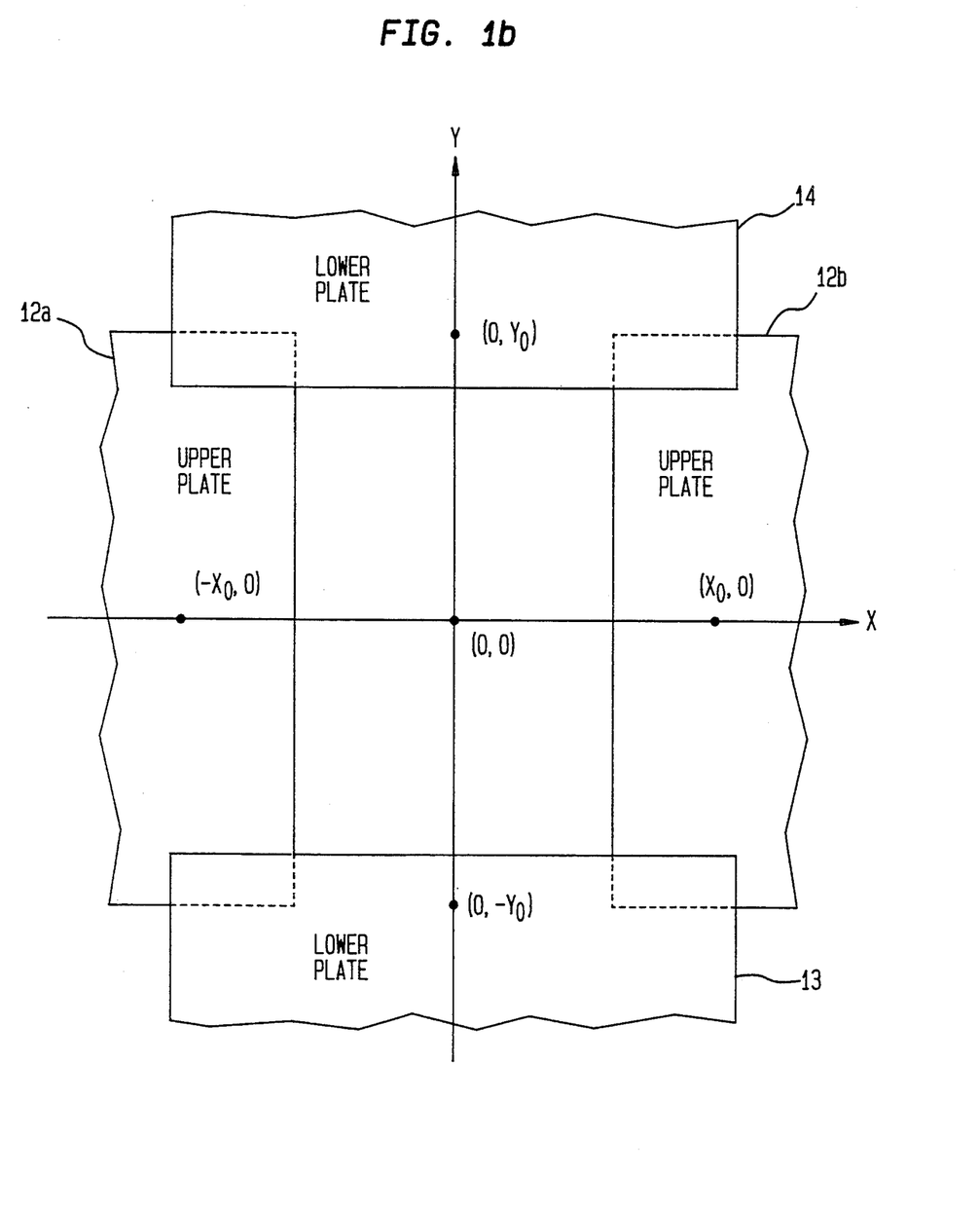

In the exemplary embodiments of the invention described below, the processor 21 moves the plates 12a, 12b, 13 and 14 with fixed velocities and periodically determines desirable radiation beam intensities according to these equations. During each of the treatment schemes described below, only one of the plates 12a, 12b, 13 and 14 is in motion at any given time.

Alternatively, the intensity of the radiation beam may be held constant over the treatment and the plates may be moved with variable velocities to produce a non-linear beam profile. To generate a rotationally symmetric beam profile, for example, the equations 15 and 16 may be solved for $v_x$ and $v_y$. In this alternative embodiment, the processor 21 causes actuator 19 to periodically move the plates to positions which produce the desired velocity profile.

The first treatment to be described produces a parabolic dose distribution. All of these treatments describe positioning of the jaws 12a, 12b, 13 and 14. This positioning may be more readily understood with reference to FIG. 1b.

In order to apply this first treatment, the apparatus is initially set up with the flattening filter 5 in place, and the lower collimator plates 13, 14 positioned at edges of the beam field symmetrically placed about the X axis at coordinates $(X=0, Y=-Y_0)$ and $(X=0, Y=+Y_0)$, respectively, where $Y_0$ is a constant. These plates are held in this position during the first section of the treatment, and for the purposes of the treatment, may be considered "fully open." While plates 13 and 14 may be physically capable of opening further, the positions $Y_0$ and $-Y_0$ define a preferred beam width. Opening the jaws 13 and 14 any wider this would result in undesirable irradiation of surrounding tissues.

Upper plate 12a is initially placed along the X axis at $(X=-X_0, Y=0)$, where $X_0$ is a constant. Upper plate 12b is placed at the origin (i.e. $X=0$ and $Y=0$). Plate 12b is held motionless at the origin, while Plate 12a is moved towards plate 12b by the actuator 19, under control of the processor 21. It is understood that the application of a radiation beam with constant jaw velocity during this motion would result in the known wedge shaped isodose contour. Instead, during this portion of the treatment, the intensity of the radiation beam is governed by equation (15). The result is that the isodose contour has the desired parabolic cross section, with the maximum radiation dosage at the origin, and zero dosage at $(X=-X_0)$.

Once the two plates meet at the origin, the beam is completely blocked. The irradiation of the half of the treatment area for which X is less than zero is complete for the first half (with $Y=a$ constant) of the treatment. The treatment may optionally be interrupted at this point with no effect on the total dosage received at any point.

During the next portion of the irradiation, plate 12a is held motionless, while plate 12b moves away from plate 12a in the positive X direction. The intensity of the radiation beam during this part of the treatment is again controlled by the processor 21 to follow equation (15). The second portion of the irradiation deposits a beam profile on the positive side of the X axis, completing the desired parabolic cross section, with the maximum radiation dosage at the origin, and zero dosage at $(X=+X_0)$. When plate 12b reaches the point $(X=+X_0, Y=0)$, the radiation is again interrupted by, for example, conditioning the accelerator 104 to provide no electron beam pulses or by closing a shutter to block the electron beam $e^-$. The first half of the treatment, in which the positions of plates 13, and 14 are held constant, is complete.

To set up for the second half of the treatment, the upper plate 12a is returned to $(X=-X_0, Y=0)$, "fully opening" the upper plates 12a and 12b. These plates will be motionless in the second half of the treatment. As in the first half of the treatment, the motionless plates are only opened enough to irradiate the zone to be treated so that surrounding tissues are not subjected to unnecessary irradiation.

Lower plate 14 is moved to the origin and lower plate 13 is initially left at its open position at $(X=0, Y=Y_0)$. Plate 14 is held motionless at the origin, while Plate 13 is actuated towards plate 14. During this portion of the treatment, the intensity of the radiation beam is governed by equation (16). The isodose contour has the desired parabolic cross section, with the maximum radiation dosage at the origin, and zero dosage at $(Y=-Y_0)$.

Once the two plates meet at the origin, the beam is completely blocked. The irradiation of the half of the treatment area for which Y is less than zero is complete for the second half of the treatment (with $X=a$ constant).

During the last portion of the irradiation, plate 13 is held motionless at the origin, while plate 14 moves away from plate 13 in the positive Y direction. The intensity of the radiation beam during this part of the treatment is again controlled to follow equation (16). The last portion of the irradiation deposits a beam profile on the positive side of the Y axis, completing the desired parabolic cross section, with the maximum radiation dosage at the origin, and zero dosage at $(Y=+Y_0)$. When plate 14 reaches the point $(X=0, Y=+Y_0)$, the radiation is interrupted and the treatment is complete.

A second embodiment of the invention for depositing the desired parabolic isodose profile may be used to overcome hardware limitations on the radiation treatment apparatus which restricts the motion of the lower plates. In the second method, the lower plates may have limited ability to move, or they may even be fixed.

In this embodiment of the invention, the first half of the treatment is performed with the lower plates 13, 14 fixed, while the intensity of the radiation beam and the motion of plates 12a, 12b is defined by equation (15), as in the first embodiment. At the completion of the first half of the treatment, the radiation is interrupted, the upper plates 12a, 12b are returned to their original positions, and the lower plates 13, 14 remain open. The lower part of collimator assembly 105 is rotated ninety degrees by the actuator 22, responsive to the processor 21, so that the upper plates 12a, 12b are positioned along the Y axis, and the lower plates are symmetrically placed about the X axis. The second half of the treatment follows the beam intensities and plate motions governed by equation (16), as in the first embodiment. In this second half of the treatment, however, it is the plates 12a and 12b which are moved.

The second embodiment may have advantages over the first embodiment for a beam forming apparatus which has a rotatable collimator. Because the upper plates are closer to the radiation source, movement of an upper plate effects a greater change in the width of the beam (in the plane of the treatment area) than does movement of a lower plate through the same distance. Since the upper 12a, 12b and lower 13, 14 plates are typically actuated by the same type of equipment, they are each capable of being actuated at the same maximum plate velocity. Therefore, the upper plates 12a, 12b are capable of increasing or decreasing the width of the beam by a desired amount faster than the lower plates 13, 14 can. In addition, control of the apparatus may be simplified in a system having a rotating collimating assembly, since only one pair of numerically controlled actuators 19 is needed to actuate the one set of plates for this device.

It is understood by practitioners in the field that the particular parabolas defined by equations (12) and (13) are exemplary in nature and that a number of variations are mathematically possible. The use of these parabolic contours, rotationally symmetric about the origin is made to simplify the plate movements used to achieve a number of desired isodose contours. For example, one or both of the parabolic contours could be offset from the origin by a constant displacement. This would require both plates in one or both sets of plates to be capable of crossing the axis. Although this is technically feasible, it may be more practical to move the object being treated and keep the beam center at the origin than to electronically offset the beam profile center.

A third embodiment uses the general teachings of the earlier described embodiments to extend the capabilities of the invention even further. In this embodiment, the collimator 105 does not require a flattening filter 5. Instead, the motions of the collimator plates 12, 13, 14 are controlled to produce a beam profile whose isodose contours are approximately flat. That is to say, any isodose contour will lie in a plane parallel to the treatment surface. Using this method, the radiation output of the electron accelerator is not decreased by filter attenuation, so that for a given accelerator, higher radiation intensity may be applied to the treatment area. This method may have many applications ranging from pencil beam treatment to whole body radiation.

Figure 4:
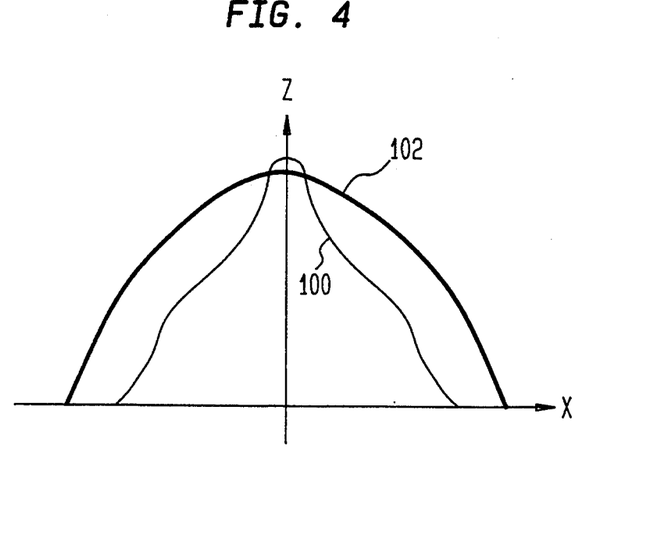

FIG. 4 shows the beam profile 100 produced with both collimator plates open, when the flattening filter 5 is removed (hereinafter referred to as the "raw beam" profile). The raw beam profile 100 may have an arbitrary form, and will vary with the apparatus used. This profile is empirically determined. For typical raw beams, the isodose curve may be approximated by finding a best-fit parabolic curve 102. The parabolic curve 102 is exaggerated in the Figure to clearly distinguish it from the raw beam profile 100. In order to apply a uniform dosage with the raw beam, it is necessary to expose the areas further from the origin to the beam longer than the center is exposed to the beam. That is to say, a compensating beam profile that is complementary to the parabolic isodose curve of the raw beam 100 is needed.

Figure 5A:
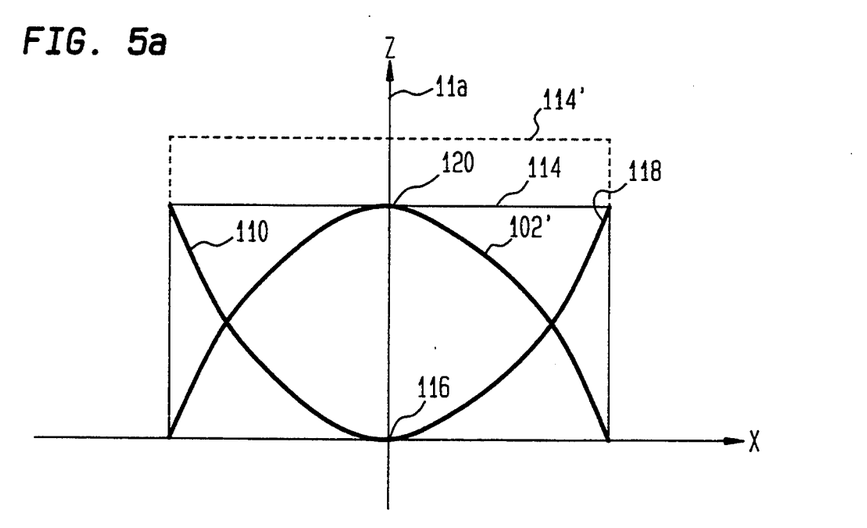
FIG. 5a is a graph of an isodose curve which shows a flattened beam profile generated by the system shown in FIG. 1.

FIG. 5a shows how a compensating isodose curve 110 is added to the raw beam isodose curve 102' to provide a flat profile 114. FIG. 5a shows clearly that the compensating isodose curve 110 is greatest at the edges of the beam 118, and smallest at the beam axis 116. The smallest total flat beam isodose profile achievable is the dose 120 detected at the beam axis 11a for the raw beam isodose curve 102'. Mathematically, the compensating isodose curve 110 is the difference produced by subtracting the raw beam isodose curve 102' from the flat beam curve 114. To produce this compensating beam profile 110, the compensating dosage at the edge of the beam is desirably the raw beam maximum value 120, and the compensating dosage must fall off to zero at the center 11a of the beam. The upper dose limit is determined by the maximum raw beam intensity 120 and the available plate speeds.

It is understood by one skilled in the art that a flat profile with a higher total isodose curve 114' may be achieved by extending the amount of time that the plates spend in any one position.

The desired flat beam profile is defined by $z = F$, where F is constant for any dosage. The raw beam isodose profile is defined by the measured values of $z_r(x,y)$, which are fitted to the form of equation (17). The compensating function $z_c(x,y)$ is the difference of the two.

$$z_r(x,y) = K - a*(x^2 + y^2) \qquad (17)$$

where K is a constant.

The beam attenuation through a solid medium is defined by equation (2). Substituting in the equation for $z_r(x,y)$ yields equation (18).

$$D_{0(x,y)} = D_a e^{\mu[F - K + a(x^2 + y^2)]} \qquad (18)$$

Differentiating with respect to time to get the dose rate equation yields equation (19).

$$\dot{D}_{0(x,y)} = D_a \mu e^{\mu[F - K + a(x^2 + y^2)]} |\{2axv_x + 2ayv_y\}| \qquad (19)$$

As was done for the first embodiment of the invention, this equation is separated into functions of X only and Y only yielding equations (20) and (21) governing the plate motions.

$$\dot{D}_{01(x)|y=const.} = D_a \mu [e^{\mu(F - K + ay^2)}] * e^{\mu ax^2} 2axv_x \qquad (20)$$

$$\dot{D}_{02(y)|x=const.} = D_a \mu [e^{\mu(F - K + ax^2)}] * e^{\mu ay^2} 2ayv_y \qquad (21)$$

As noted above, in order to move the collimator plates to furnish the beam profile defined by equations (20) and (21), the treatment area must be exposed to the edges of the beam longer than the center of the treatment area (at the beam axis). As shown in FIGS. 2a and 2b, during any dynamic beam forming treatment, the region under the stationary plate is exposed to the more intense radiation.

In contrast to the parabolic beamform generation in the first and second embodiments of the invention, flat beam generation shown in FIG. 5a requires that the stationary plate be stationed at the outer edge of the beam instead of at the beam center. In order to accomplish this, both plates in at least one set of collimator plates 12a, 12b are capable of crossing the axis.

In order to apply the treatment, the apparatus is first set up with the lower collimator plates 13, 14 positioned at edges of the beam field symmetrically placed about the X axis at coordinates ($X=0$, $Y=-Y_0$) and ($X=0$, $Y=+Y_0$), respectively, where $Y_0$ is a constant. These plates are held steady during the first section of the treatment.

Figure 5B:
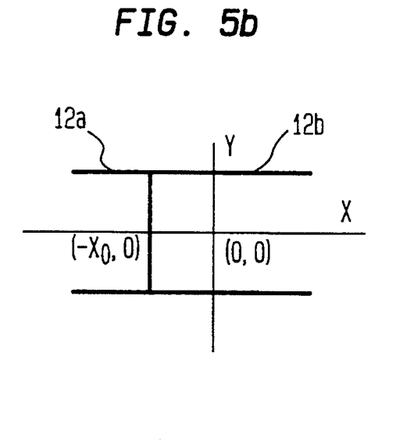

As shown in FIG. 5b, upper plates 12a and 12b are both initially placed along the X axis at ($X=-X_0$, $Y=0$). Plate 12a is held motionless at the edge of the desired beam, while Plate 12b is actuated towards the origin, increasing the width of the beam. During this portion of the treatment, the intensity of the radiation beam is governed by equation (20).

Figure 5C:
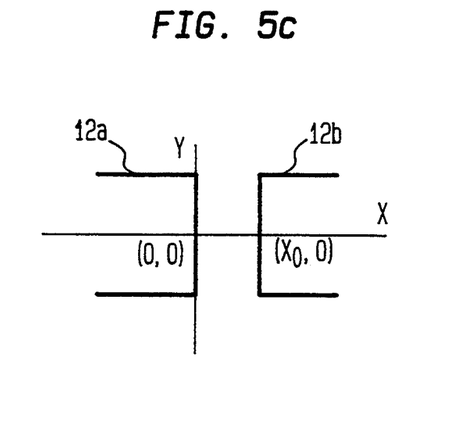

Once plate 12b reaches the origin, the treatment is interrupted. The irradiation of the portion of the treatment area for which X is less than zero and Y is a constant is complete. Next, as shown in FIG. 5c, plate 12a is positioned at the origin and plate 12b is moved to ($X = +X_0$, $Y=0$) before beginning the next portion of the treatment.

During the next portion of the irradiation, plate 12b is held motionless, while plate 12a moves towards 12b in the positive X direction, decreasing the beam width. The intensity of the beam during this part of the treatment is again controlled to follow equation (20). The second portion of the irradiation deposits a beam profile on the positive side of the X axis, completing the desired flat beam. When plate 12b reaches the point ($X = +X_0$, $Y=0$), the plates have closed and the radiation is interrupted. The first half of the treatment, in which the positions of plates 13, and 14 are held constant, is complete. It should be noted that both plates 12a and 12b cross the beam axis during the first half of the treatment.

The upper plate 12a is returned to ($X = -X_0$, $Y=0$), "fully opening" the upper plates. As in the first half of the treatment, the motionless plates are only opened up enough to irradiate the zone to be treated, and surrounding tissues are not subjected to irradiation. Lower plates 13 and 14 are both moved to ($X=0$, $Y=-Y0$) a closed position, prior to beginning the second half of the irradiation.

From this point on, the half of the treatment with the upper plates fixed proceeds in the same manner as the prior treatment when the lower plates were held still. Plate 13 is held motionless at the edge of the beam, while Plate 14 is actuated away from plate 13. During this portion of the treatment, the intensity of the X ray beam is governed by equation (21). The isodose contour has the desired flat profile.

Once the plate 14 reaches the origin, the treatment is interrupted. The irradiation of the half of the treatment area for which Y is less than zero and X is constant is complete. Plate 13 is moved to the origin and plate 14 is moved to the edge of the beam at ($X = +X_0$, $Y=0$) before resuming treatment.

During the last portion of the irradiation, plate 14 is held motionless, while plate 13 moves towards plate 13 in the positive Y direction. The intensity of the beam during this part of the treatment is again controlled to follow equation (21). The last portion of the irradiation deposits a flat beam profile on the positive side of the Y axis, completing the treatment. The result is that the isodose contour has the desired flat profile.

It is understood by one skilled in the art that a flat profile with a higher total dosage 114' may be achieved by reducing the velocities $v_x$ and $v_y$ resulting in the plates being held in each position for a longer period of time.

Furthermore, it should be understood by those skilled in the art that other movements of the aperture plates 12a, 12b, 13 and 14 could produce the same result. For example, in FIG. 5c, both plates 12a and 12b could start at position (0, +X0) and plate 12a could be moved away from plate 12b.

A fourth embodiment of the invention produces a flat beam profile using only one pair of movable plates. In the previous embodiment, both plates of the pair are able to be moved across the beam axis. In this fourth method, the lower plates may have limited ability to move, or they may even be fixed.

In this embodiment of the invention, the first half of the treatment is performed with the lower plates 13, 14 fixed, and the intensity of the radiation beam is defined by equation (20), as in the third embodiment. At the completion of the first half of the treatment, the radiation is interrupted, the upper plates 12a, 12b are returned to their original positions while the lower plates 13, 14 remain open. The lower part of collimator assembly 105 is rotated ninety degrees, so that the upper plates 12a, 12b are positioned along the Y axis, and the lower plates are symmetrically placed about the X axis. The second half of the treatment follows the beam intensity and plate motions governed by equation (20), as in the third embodiment.

The fourth embodiment, like the rotationally symmetric beam profile with collimator rotation, may have advantages over moving the lower plates in a system with a rotatable collimator. Since the flat beam generation requires the collimator plates to cross the beam axis, the plate actuating hardware is more complex than for a more general beam profile. It is therefore a distinct advantage to use only one set of movable plates.

It is understood by one skilled in the art that many variations of the embodiments described herein are contemplated. While the invention has been described in terms of exemplary embodiments, it is contemplated that it may be practiced as outlined above with modifications within the spirit and scope of the appended claims.

What is claimed is:

1. A method for applying a desired radiation treatment in a system having: 1) a radiation source which generates a radiation beam having an intensity along an axis and 2) a collimator assembly having a plurality of independently movable sets of plates disposed in the path of the radiation beam and oriented in a direction perpendicular to said beam axis, each set having two movable plates, the method comprising the steps of:
   a) defining a continuous and continuously derivable function to control the intensity of the radiation beam as a function of plate position to achieve said desired radiation treatment having any desired isodose curve and without the use of rotation of the path of said radiation beam;
   b) actuating each of said plates independently during the treatment, at a respective predetermined velocity to cause sad beam to change in width and intensity over time in accordance with said function so as to produce the desired radiation treatment.

2. The method of claim 1, further comprising the step of positioning both plates such that at least one set of movable plates defines an opening on one side of the beam axis during the treatment.

3. A method for applying a desired radiation treatment with a rotationally symmetric isodose profile in a system having: 1) a radiation source which generates a radiation beam having an intensity along an axis and 2) a collimator assembly having a plurality of sets of independently movable plates disposed in the path of the radiation beam and oriented in a direction perpendicular to said beam axis, each set having two movable plates, the method comprising the steps of:
   a) selecting a set of movable plates;
   b) generating control signals for actuating said selected set of plates;
   c) positioning a first plate in the selected set at the axis and a second plate in the selected set at a predetermined distance form said axis;
   d) actuating said selected set of plates during the treatment, in response to said control signals, causing said beam to change in width, comprising the steps of;
      1) actuating the second plate in the selected set to meet the first plate at the axis;

2) interrupting the radiation when the plates meet;
3) continuing the radiation while actuating the first plate to move away form the second plate;
4) interrupting the treatment when the second plate is separated form the first plate by the predetermined distance;

e) positioning one of said plurality of sets of movable plates for moving in a second direction perpendicular to the first direction; and f) repeating step (d) for said positioned set of plates.

4. The method set forth in claim 3, in which step (e) comprises the steps of:
returning the plates to their respective starting positions as defined at step c); and
rotating the collimator assembly ninety degrees.

5. The method set forth in claim 3, in which step (e) comprises the steps of:
selecting a further set of movable plates mounted orthogonal to said set of movable plates; and
positioning a first plate in the selected further set at the axis an a second plate in the set at a predetermined distance from said axis.

6. A method for applying radiation treatment with a flat isodose profile in a system having: 1) a radiation source which generates a radiation beam having an intensity along an axis and 2) a collimator having a plurality of sets of independently movable plates disposed in the path of the radiation beam and oriented in a direction perpendicular to said beam axis, each set having two movable plates, the method comprising the steps of:

a) selecting a set of movable plates;
b) generating control signals for actuating said selected set of plates;
c) positioning first and second plates within the selected set together at a starting position a predetermined distance from the beam axis and on a first side of the axis;
d) actuating said selected set of plates during the treatment, in response to said control signals, causing said beam to change in width, comprising the steps of;
1) actuating the first plate in the selected set to move towards the axis;
2) interrupting the radiation when the first plate reaches the axis;
3) positioning the plates to meet at said predetermined distance on a second side of the axis, opposite to the first side;
4) actuating the second plate in the selected set to move towards the axis;
5) interrupting the treatment when the second plate reaches the axis;

e) positioning one of said plurality of sets of movable plates for moving in a second direction perpendicular to the first direction; and f) repeating step (d) for said positioned set of plates.

7. The method set forth in claim 6, in which step (e) comprises the steps of:
returning the selected plates to the starting position as defined by step b); and
rotating the collimator assembly by ninety degrees.

8. The method set forth in claim 6, in which step (e) comprises the steps of:
selecting a further set of movable plates mounted orthogonal to said set of movable plates; and
positioning plates within the further set as set forth in step b).

9. A method in accordance with claim 6, in which there is a distance between said plates, the method further comprising the step of defining a function to control the intensity of the radiation beam as a function of plate position so that the intensity increase when the distance between the plates decreases.

10. A method for applying a desired radiation treatment with a parabolic isodose profile in a system having: 1) a radiation source which generates a radiation beam having an intensity along an axis and 2) a collimator assembly having at least one st of independently movable plates disposed in the path of the radiation beam and oriented in a direction perpendicular to said beam axis, said set having two plates, the method comprising the steps of:

a) defining a function to control the intensity of the radiation beam as a function of plate position to achieve said desired radiation treatment;
b) positioning a first plate in the set at the axis and a second plate in the set at a predetermined distance from said axis;
c) generating control signals for actuating said set of plates;
d) actuating said set of plates during the treatment, in response to said control signals, causing said beam to change in width, comprising the steps of;
1) actuating the second plate in the set of plates to meet the first plate at the axis;
2) stopping the radiation when the first and second plates meet;
3) restarting the radiation while actuating the first plate to move away form the second plate; and
4) stopping the treatment when the second plate is separated from the first plate by the predetermined distance.

11. A method in accordance with claim 10, in which said first and second plates are moved with a constant velocity during respective steps (1) and (3).

12. A method in accordance with claim 10, in which step (a) includes the step of defining said function to achieve an isodose profile which is continuous and continually derivable.

13. A method in accordance with claim 10, in which there is a distance between said pates and step (a) includes the step of defining said function to increase the radiation beam intensity when the distance between said plates decreases.

14. A method in accordance with claim 10, further comprising the following steps:
returning the plates to their respective starting positions as defined at step (b);
rotating the collimator assembly ninety degrees; and
repeating steps (c) and (d).

15. A method in accordance with claim 10, in which the system includes third and fourth independently movable plates, the method further comprising the following steps:
positioning said third and fourth plates prior to executing step (c), so that each is located at a further predetermined distance from said axis;
positioning the first and second plates within said set after executing step (d), so hat each is located at said predetermined distance from said axis;
positioning the third plate at the axis and the fourth plate at said further predetermined distance form said axis;

actuating said third and fourth plates, in response to said control signals, causing said beam to change in width, comprising the steps of;

1) actuating the fourth pate to meet the third plate at the axis;
2) interrupting the radiation when the third and fourth plates meet;
3) continuing the radiation while actuating the third plate to move away from the fourth plate; and
4) stopping the treatment when the fourth plate is separated from the third plate by said fourth predetermined distance.

16. A method for applying a desired radiation treatment to a predetermined area using a system having: 1) a radiation source which generates a radiation beam having an intensity along an axis and 2) a collimator assembly having a beam flattening filter and at least one set of independently movable plates disposed in the path of the radiation beam and oriented in a direction perpendicular to said beam axis, said set having two movable plates, the method comprising the steps of:

a) defining a function to control at least one of the intensity of the radiation beam and the velocity of said plates to achieve said desired radiation treatment, said treatment having a continuous and continually derivable isodose profile with an inflection point approximately coincident with a center point of the predetermined area;

b) actuating each of said plates in accordance with aid function independently during the treatment, to cause said beam to change in width over time; and
c) controlling said radiation source in accordance with said function to cause said beam to change in intensity over time to produce the desired treatment.

17. A method for applying a desired radiation treatment to a predetermined area using a system having: 1) a radiation source which generates a radiation beam having an intensity along an axis and 2) a collimator assembly having at least one set of independently movable plates disposed in the path of the radiation beam and oriented in a direction perpendicular to said beam axis, said set having two movable plates, the method comprising the steps of:

a) defining a function to control at least one of the intensity of the radiation beam and the velocity of said plates to achieve said desired radiation treatment, said desired radiation treatment having a continuous and continually derivable isodose profile which is at least as great at the edge of the are as in the center of the area;
b) actuating each of said plate sin accordance with said function independently during the treatment, to cause said beam to change in width over time; and
c) controlling said radiation source in accordance with said function to cause said beam to change in intensity over time to produce the desired radiation treatment.

* * * * *

UNITED STATES PATENT AND TRADEMARK OFFICE
CERTIFICATE OF CORRECTION

PATENT NO. : 5,332,908

DATED : July 26, 1994

INVENTOR(S) : Weidlich

It is certified that error appears in the above-identified patent and that said Letters Patent is hereby corrected as shown below:

Column 14

Line 41    delete "sad"
                     and insert --said--

Line 62    delete "form:
                     and insert --from--

Column 15

Line 5     delete "form"
                     and insert --from--

Line 21    delete "an"
                     and insert --and--

Column 16

Line 5     delete "increase"
                     and insert --increases--

Line 11    delete "st"
                     and insert --set--

Line 64    delete "hat"
                     and insert --that--

Line 68    delete "form"
                     and insert --from--

UNITED STATES PATENT AND TRADEMARK OFFICE
CERTIFICATE OF CORRECTION

PATENT NO. : 5,332,908
DATED : July 26, 1994
INVENTOR(S) : Weidlich

It is certified that error appears in the above-indentified patent and that said Letters Patent is hereby corrected as shown below:

<u>Column 17</u>

Line 4    delete "pate"
                     and insert --plate--

<u>Column 18</u>

Line 1    delete "aid"
                     and insert --said--

Line 22   delete "are"
                     and insert --area--

Line 24   delete "plate sin"
                     and insert --plates in--

Signed and Sealed this

First Day of November, 1994

*Attest:*

BRUCE LEHMAN

*Attesting Officer*        *Commissioner of Patents and Trademarks*